United States Patent [19]

Markowitz

[11] Patent Number: 5,238,006
[45] Date of Patent: Aug. 24, 1993

[54] APNEA STIMULATION LEAD
[75] Inventor: H. Toby Markowitz, Roseville, Minn.
[73] Assignee: Medtronic, Inc., Minneapolis, Minn.
[21] Appl. No.: 719,929
[22] Filed: Jun. 24, 1991
[51] Int. Cl.$^5$ ............................................... A61N 1/00
[52] U.S. Cl. .................................. 607/143; 128/642; 174/117 FF
[58] Field of Search ............... 128/784, 639, 640, 644, 128/419 P, 642, 785, 786; 174/102 SP, 117 F, 117 FF, 727 R, 117 A, 257, 268, 74 R, 84 R, 88 R, 94 R

[56] References Cited

U.S. PATENT DOCUMENTS

| | | | |
|---|---|---|---|
| 2,972,657 | 2/1961 | Stemke | 174/94 R |
| 3,259,873 | 7/1966 | Parkinson et al. | 174/88 R |
| 3,268,846 | 8/1966 | Morey | 174/117 FF |
| 3,876,964 | 4/1975 | Balaster et al. | 174/268 |
| 4,133,735 | 1/1979 | Afromowitz et al. | 128/642 X |
| 4,353,372 | 10/1982 | Ayer | 128/640 |
| 4,370,984 | 2/1983 | Cartmell | 128/641 |
| 4,506,666 | 3/1985 | Durkan . | |
| 4,570,631 | 2/1986 | Durkan . | |
| 4,586,106 | 4/1986 | Frazier | 361/212 |
| 4,659,872 | 4/1987 | Dery et al. | 174/117 A |
| 4,748,293 | 5/1988 | Kikuchi et al. | 174/117 FF |
| 4,830,008 | 5/1989 | Meer . | |
| 4,831,240 | 5/1989 | Davis | 174/94 R |

FOREIGN PATENT DOCUMENTS 0404427 12/1990 European Pat. Off. .

OTHER PUBLICATIONS

Glenn, William W. L., Diaphragm Pacing: Present Status, 1977.
Cook, William R., & Osguthorpe, J. David, Obstructive Sleep Apnea: Diagnosis and Treatment, Dec. 1985.

Primary Examiner—Lee S. Cohen
Assistant Examiner—Samuel Gilbert
Attorney, Agent, or Firm—John L. Rooney

[57] ABSTRACT

A stimulation lead for electrically coupling an implantable pulse generator to an electrode in an apnea treatment system and method of making same. The lead employs a thin substrate of polyurethane or other highly flexible implantable material. Conductors are placed on the substrate by silk screening a conductive ink. The ends of the lead are electrically terminated using rivets which couple through the substrate. The substrate is folded to enclose the conductors, thereby insulating them and protecting them from bodily fluids. Suitable connectors may be attached to either end. The resulting lead is easily fabricated and is extremely thin and flexible.

7 Claims, 8 Drawing Sheets

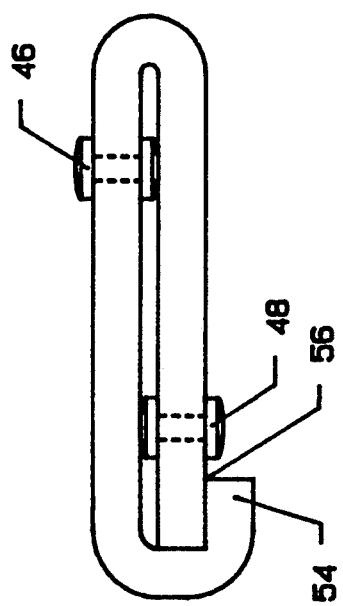

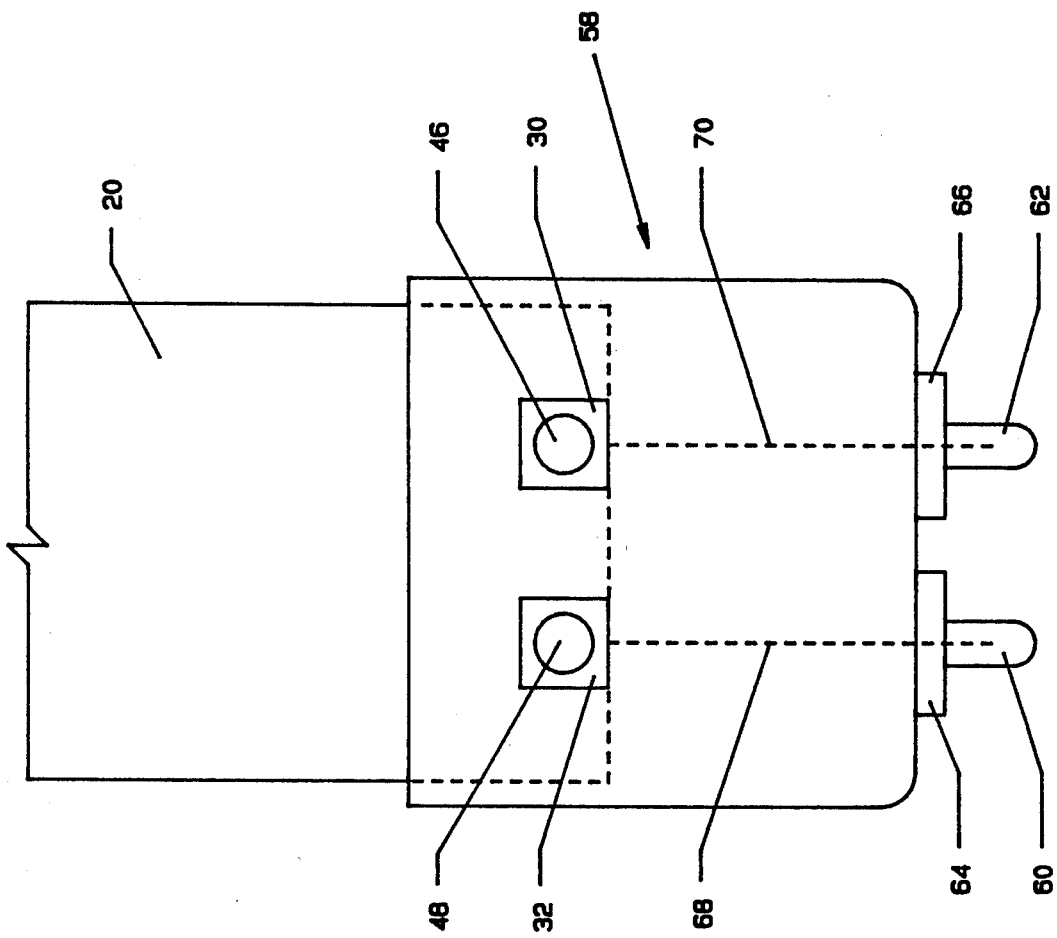

5,238,006

APNEA STIMULATION LEAD

CROSS REFERENCE TO CO-PENDING APPLICATIONS

U.S. patent application Ser. No. 07/610,854, filed Nov. 8, 1990, entitled "Muscle Tone"; U.S. patent application Ser. No. 07/639,192, filed Jan. 9, 1991, entitled "Servo Muscle Control"; U.S. patent application Ser. No. 07/617,158, filed Nov. 23, 1990, entitled "Multiple Stimulation Electrodes"; U.S. patent application Ser. No. 07/671,513, filed Mar. 19, 1991, now U.S. Pat. No. 5,146,918, entitled "Demand Apnea Control"; U.S. patent application Ser. No. 07/706,165, filed May 28, 1991, entitled "Airflow Feedback Measurements"; and U.S. patent application Ser. No. 07/679,120, filed Apr. 2, 1991, entitled "Implantable Apnea Generator with Ramp On Generator" are all assigned to the assignee of the present invention and incorporated herein by reference.

BACKGROUND OF THE INVENTION

1. Field of the Invention

The present invention relates generally to implantable medical devices, and more particularly, relates to implantable medical devices for the treatment of obstructive sleep apnea.

2. Description of the Prior Art

The medical characteristics of sleep apnea have been known for some time. There are two generally recognized forms of the disease. The first is central sleep apnea which is associated with the failure of the body to automatically generate the neuro-muscular stimulation necessary to initiate and control a respiratory cycle at the proper time. Work associated with employing electrical stimulation to treat this condition is discussed in "Diaphragm Pacing: Present Status", by William W. L. Glenn, in *Pace,* Volume I, at pages 357-370 (July – September 1978).

The second condition is known as obstructive sleep apnea. It is discussed at some length in "Obstructive Sleep Apnea: Diagnosis and Treatment", by Drs. Cook and Osguthorpe in *Journal of South Carolina Medical Association,* 81 (12): 647-651 (December 1985).

At present, a tracheostomy may be the treatment of choice for a number of patients when obstructive sleep apnea is severe, although systems employing continuous positive air pressure (CPAP) are now available. However, some interest has been displayed in electrical stimulation of the muscle tissue along the upper airway during respiration. U.S. Pat. No. 4,830,008 issued to Meer discusses a technique for electrical stimulation of the muscles of the upper airway in synchrony with the respiratory cycle. U.S. Pat. No. 4,506,666 issued to Durkan discusses such stimulation in conjunction with pressurized airflow supplied by a respirator.

As with most chronically implantable electrical stimulation systems, those directed to the treatment of obstructive sleep apnea have an implantable pulse generator remotely located from and cabled to sensors and stimulation electrodes. For the treatment of obstructive sleep apnea, this means that the implantable pulse generator is preferably located in the torso of the patient and one or more sensors and/or stimulation electrodes are located in the head. This configuration necessitates cabling which traverses the neck region.

Currently available insulated leads for cabling implantable pulse generators to sensors and electrodes tend to be cylindrical in shape and optimized for flex strength. Such insulated leads tend to produce an undesirable bulge in the neck region of patients having implantable obstructive sleep apnea stimulation systems.

SUMMARY OF THE INVENTION

The present invention overcomes the disadvantages found in the prior art by providing an obstructive sleep apnea treatment system wherein the components are electrically coupled together using an extremely flat cable of high reliability which is easy to construct. This flat cable and method of making same are particularly useful for any implantable application wherein coiled conductor construction is not required.

A thin sheet of flexible biocompatible material of the desired length is slightly scored to be easily folded into the proper shape. Compositions of various polymers have proven to be chronically stable within the implanted environment and are preferable for use as the substrate. The conductors are of a conductive ink and attached to the substrate using a silk screening process. After the conductive ink is affixed, a rivet is attached through the substrate at each end of each conductor for electrical coupling to a connector.

The substrate is folded to enclose the conductors along the length of the structure and sealed with adhesive or by heat treatment. Connectors are sealingly attached to each end of the structure. The insulated lead is attached between the implantable pulse generator and the sensors and/or electrodes at the time of implantation.

The resulting cable, as made and used in accordance with the present invention, is a highly robust structure. It has a substantially greater flex strength than prior art cables of equivalent thickness.

Various embodiments may be made using different numbers of conductors. Not all conductors need terminate at the same point.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein: FIG. 7 is an end view of the cable; and, FIG. 8 is a close up view of one end of the cable with connector attached.

DETAILED DESCRIPTION OF THE PREFERRED EMBODIMENTS

Figure 1:
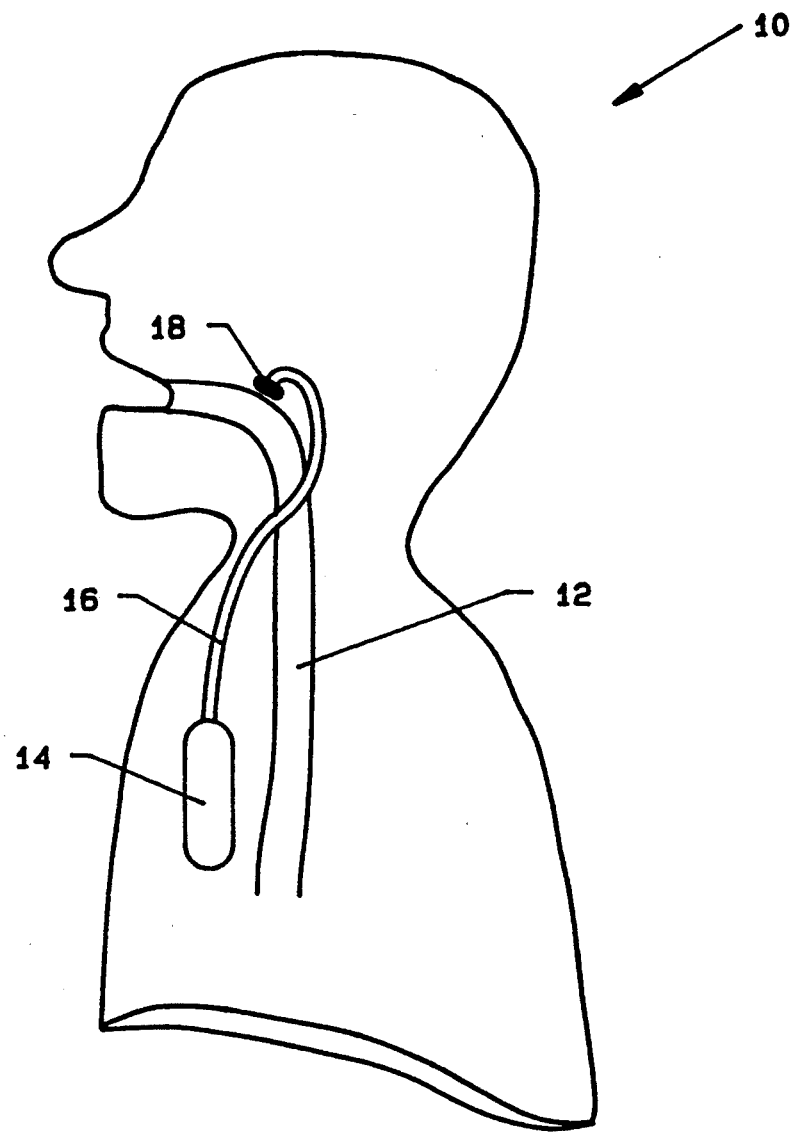
FIG. 1 is a schematic diagram of an implantable electrical stimulation system for the treatment of obstructive sleep apnea.

FIG. 1 is a schematic view of an electrical stimulation system for the treatment of obstructive sleep apnea employing the present invention implanted in patient 10. Electrode 18 is located in the musculature of the upper portion of airway 12. Implantable pulse generator 14 is electrically coupled to electrode 18 via cable 16. Because cable 16 is extremely thin, it is easily implanted in the neck of patient 10 without any prominent bulges. Although difficult to see in the drawing, the preferred method is to tunnel just under the skin from the shoulder area to the head along one side of patient 10.

For simplicity, cable 16 is shown as a two conductor cable with both conductors terminating at the same points. Those of skill in the art will be able to readily adapt the teachings found herein to embodiments having a larger number of conductors terminating at different points.

Figure 2:
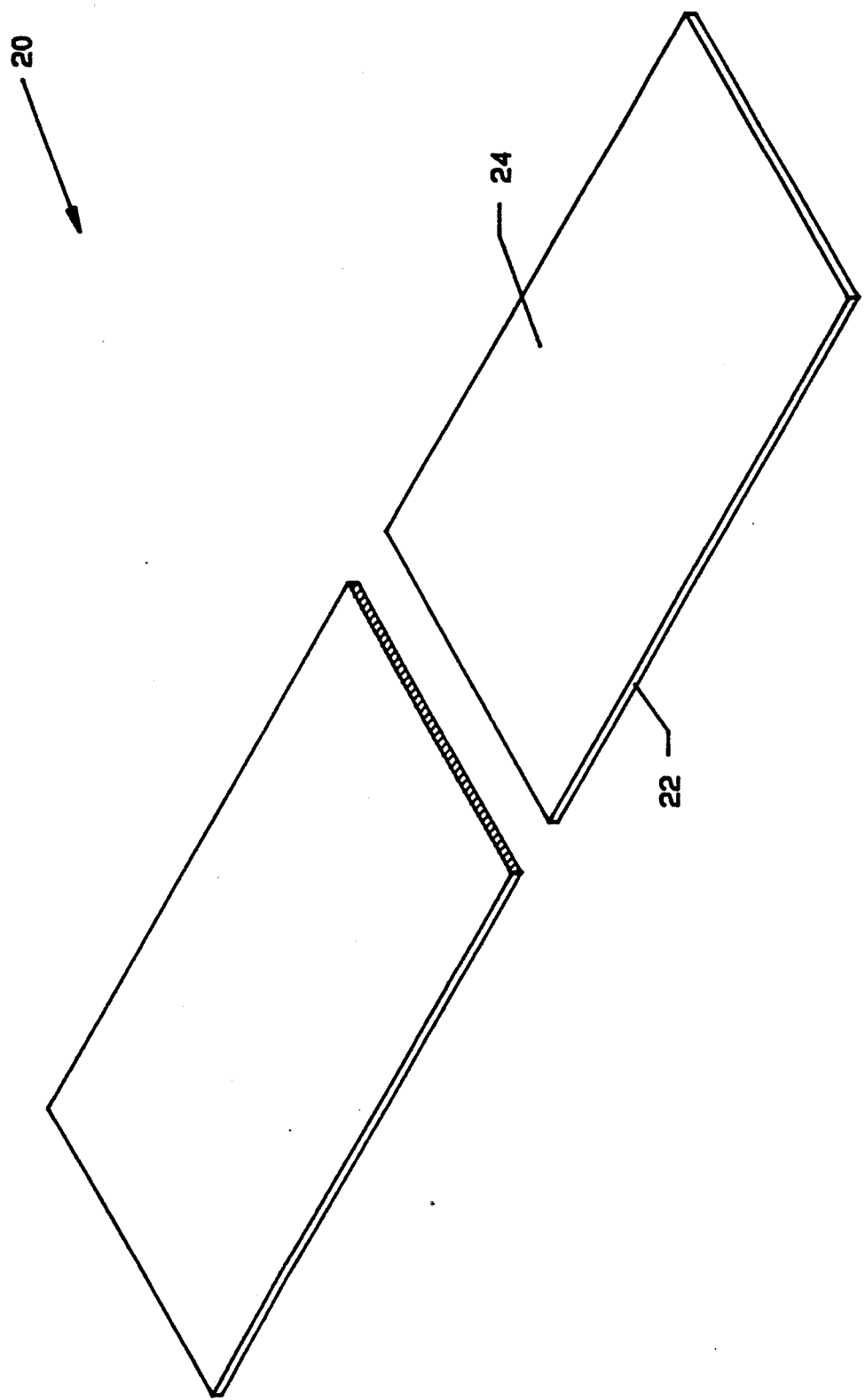
FIG. 2 is a plan view of the substrate of the cable.

FIG. 2 is a perspective view of substrate 20 of cable 16. It is preferably a sheet 24 of polyurethane or other polymer having demonstrated high flexibility and chemical stability within the environment of chronic implantation. The sheet has a length associated with the desired length of cable 16, and is slightly wider than twice the desired width as is explained in further detail below. Sheet 24 is, of course, an insulator of high dielectric constant. Because the potentials used in the typical system are relatively low, dielectric strength is not deemed to be a major factor. The thickness 22 of sheet 24 is on the order of several thousandths of an inch. Mechanical tensile and puncture strength are the most important determinants of thickness 22.

Figure 3:
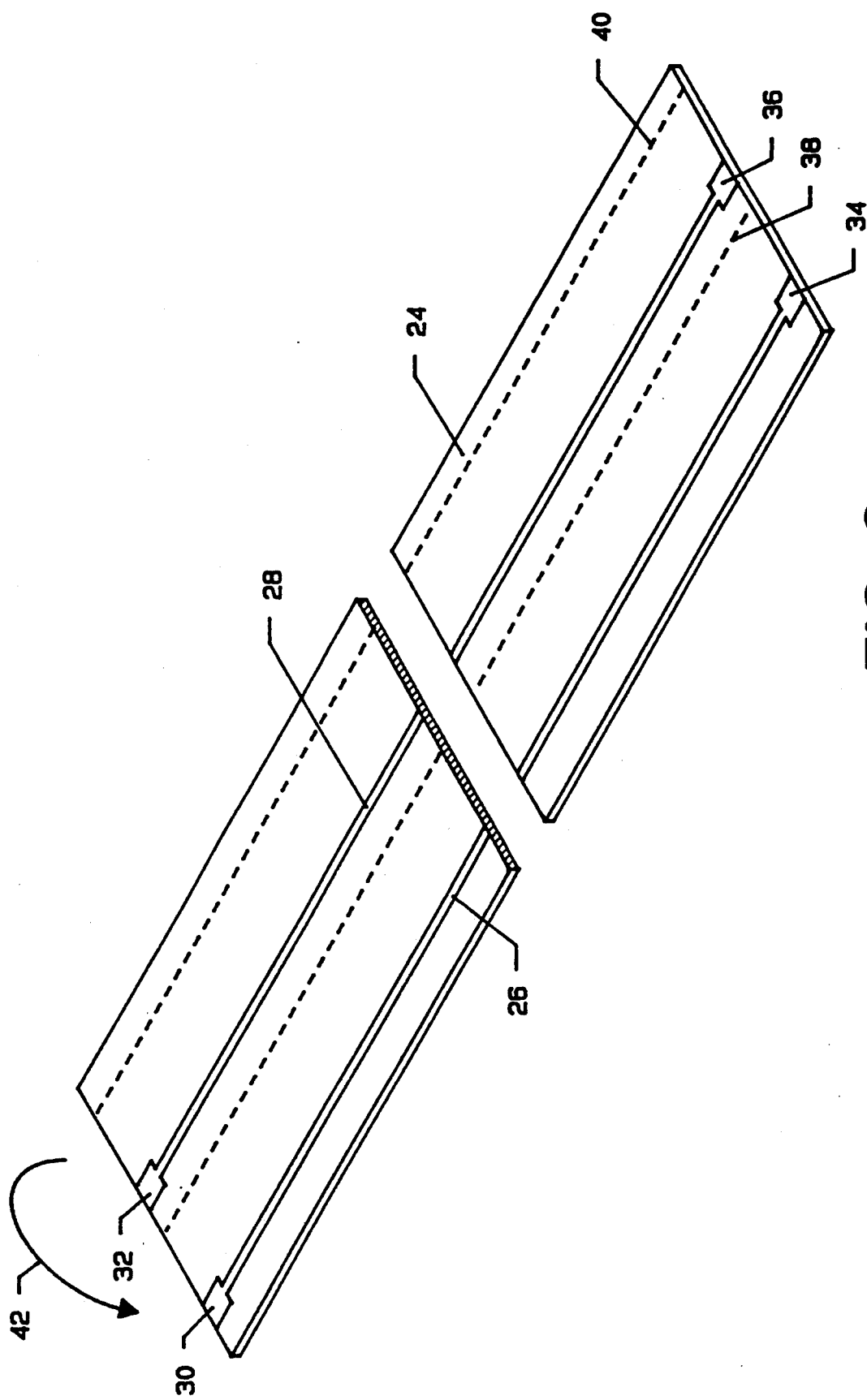
FIG. 3 is a plan view of the substrate with the conductors affixed.

FIG. 3 is a top view of sheet 24 after affixation of the conductors. Sheet 24 is lightly scored along line 38 to fold approximately in half longitudinally in the direction of arrow 42. It is also scored along line 40 to provide a sealing flap discussed in greater detail below.

Conductors 26 and 28, along with termination pads 30, 32, 34, and 36, are produced from a conductive ink which has been affixed using a silk screening process. The silk screen mask must be constructed to prevent conductors 26 and 28, termination pads 30 and 32, and termination pads 34 and 36 from coming into contact when sheet 24 is folded along line 38 in the direction of arrow 42.

Figure 4:
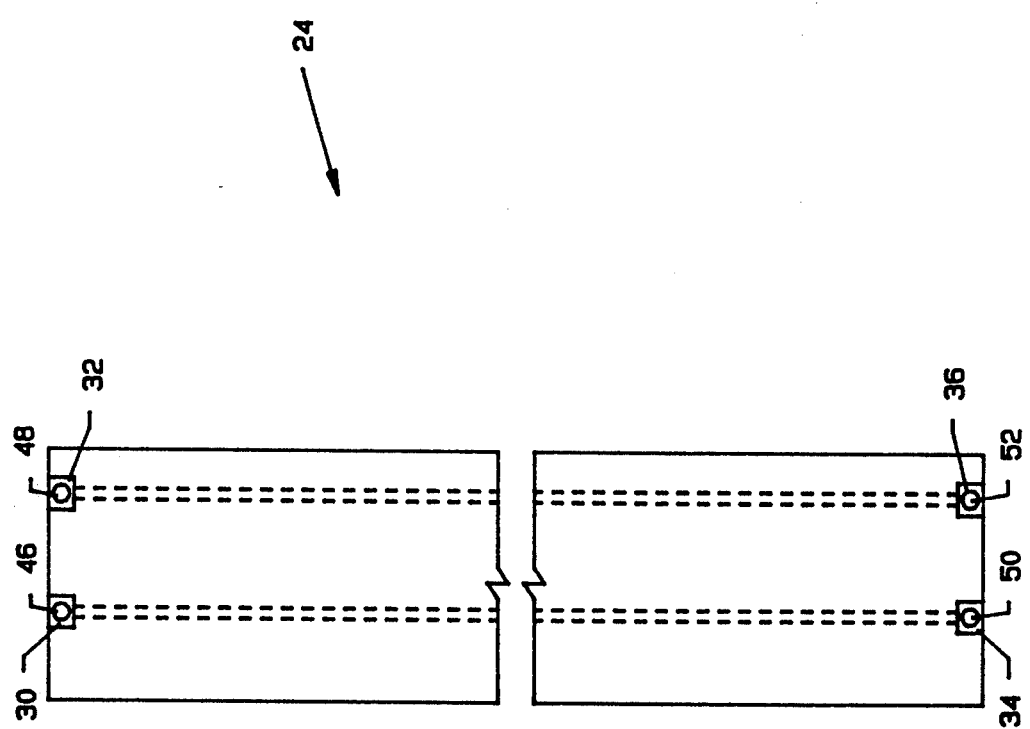
FIG. 4 is a bottom view of the cable with rivets attached.

FIG. 4 is a bottom view of sheet 24. To ensure ease in terminating each of the conductors, rivets 46, 48, 50, and 52 are affixed through sheet 24 coming into electrical contact with termination pads 30, 32, 34, and 36, respectively.

Figure 5:
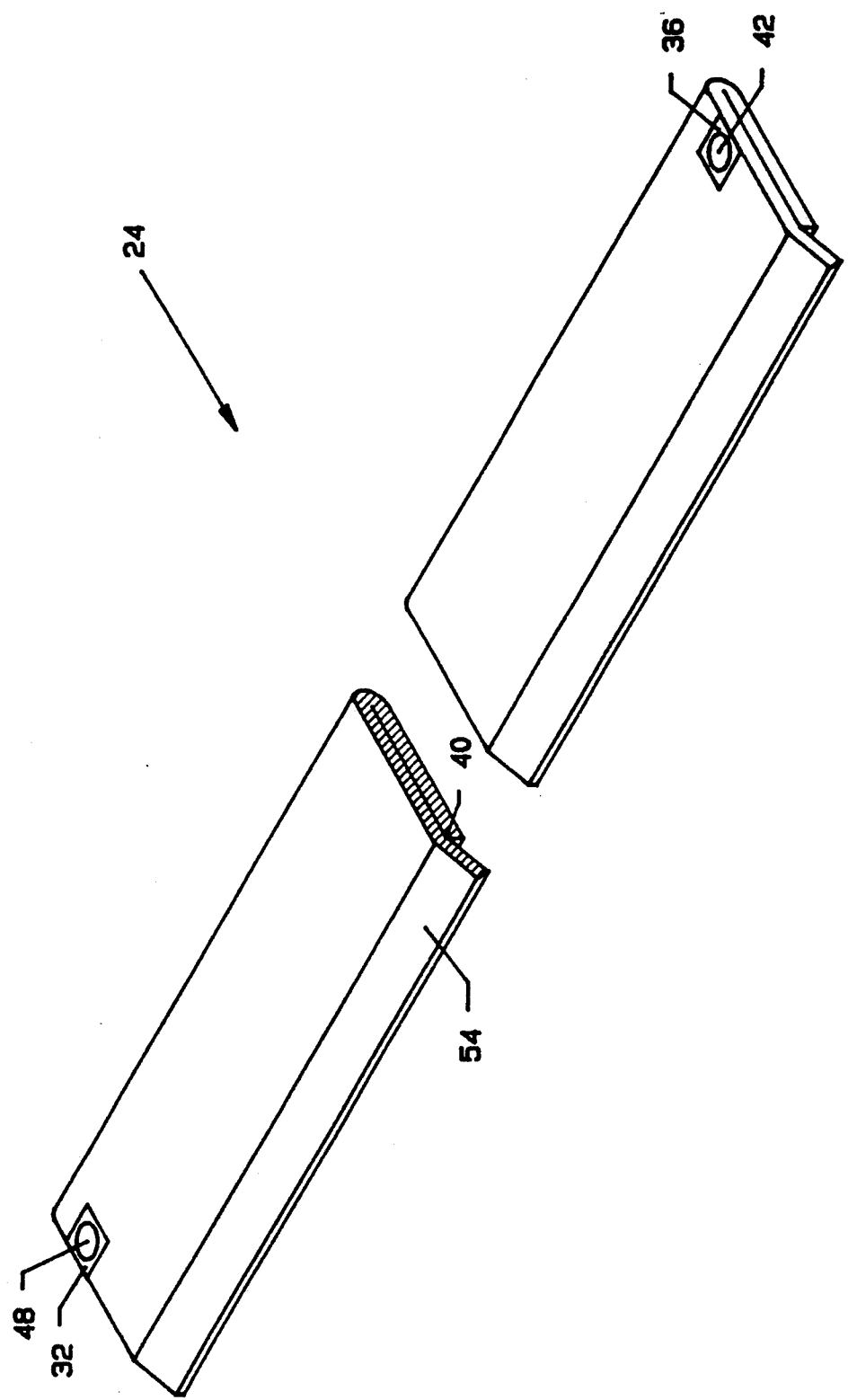
FIG. 5 is a perspective view of the cable showing the fold for sealing attachment.

FIG. 5 is a top perspective view of sheet 24 after complete folding along line 38. Sheet 24 is shown partially folded along line 40 which produces sealing flap 54. In this way, sealing flap 54 seals along the potentially open edge of cable 16. When completely folded, sealing flap 54 is sealed along its entire length by heating and/or adhesive means. Other referenced elements are as previously described.

Figure 6:
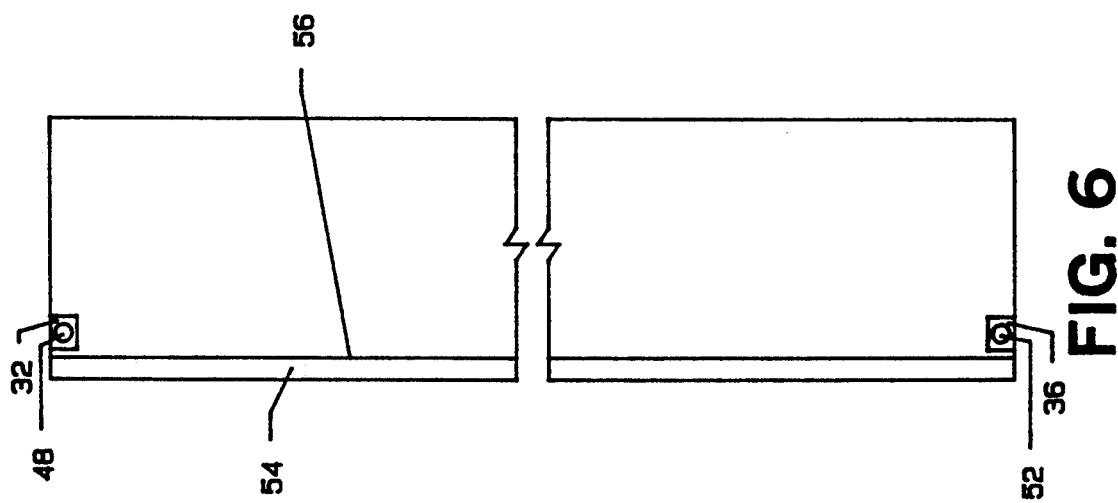
FIG. 6 is a top view of the cable.

FIG. 6 is a top view of cable 16 having sealing flap 54 completely folded and sealingly attached. Referenced elements are as previously described.

FIG. 7 is an end view of cable 16 showing sealing flap 54 sealingly attached along edge 56. All other referenced elements are as previously described.

FIG. 8 is a close up view of one end of cable 16 showing attachment of connector 58. The connector body is preferably molded from a rigid biocompatible material. Rivets 46 and 48 are welded to wires 70 and 68, respectively, which are in turn welded to terminal pins 62 and 60. In this manner, terminal pins 62 and 60 become electrically coupled to conductors 26 and 28, respectively. Gaskets 66 and 64 seal against terminal pins 62 and 60, respectively.

Having thus described the preferred embodiments of the present invention, those of skill in the art will be readily able to apply the teachings found herein to yet other embodiments of the present invention within the scope of the claims hereto attached.

I claim:

1. A body implantable cable comprising:
   a. a substrate of flexible, biocompatible, electrically insulative material with a first surface and having a proximal end and a distal end and having a crease between said proximal end and said distal end whereby a first portion of said first surface is placed adjacent a second portion of said first surface;
   b. a line of conductive ink fixedly attached between said proximal end and said distal end of said first surface of said substrate; and
   c. means for sealing said first portion and said second portion of said first surface of said substrate from the invasion of body fluids and tissue.

2. A cable according to claim 1 further comprising a rivet electrically coupled to said line and fixedly attached through said proximal end of said substrate.

3. A cable according to claim 2 further comprising a connector sealingly coupled to said substrate and electrically coupled to said rivet.

4. A body implantable cable according to claim 1, 2, or 3 wherein said first portion of said first surface contains approximately the same area as said second portion of said first surface.

5. A body implantable cable according to claim 4 wherein said substrate has a first edge and a second edge from said proximal end to said distal end and said means for sealing further comprises means coupled to said substrate for sealingly engaging said first edge to said second edge.

6. An apparatus for implantation in the body of an animal comprising:
   a. a flexible insulative substrate having a first folded surface;
   b. a conductive path of conductive ink fixedly attached to said first folded surface; and
   c. means for sealing said conductive path on said folded surface from body fluids and tissue.

7. An apparatus according to claim 6 wherein said first folded surface has a first edge and said sealing means a second edge and further comprising means coupled to said first edge and said second edge for sealingly coupling said first edge to said second edge.

* * * * *

UNITED STATES PATENT AND TRADEMARK OFFICE
CERTIFICATE OF CORRECTION

PATENT NO. : 5,238,006
DATED : August 24, 1993
INVENTOR(S) : H. Toby Markowitz

It is certified that error appears in the above-indentified patent and that said Letters Patent is hereby corrected as shown below:

Column 4, lines 54 and 55 should read "first folded surface has a first edge and a second edge and said sealing means further comprising means"

Signed and Sealed this

Twenty-third Day of August, 1994

Attest:

BRUCE LEHMAN

Attesting Officer    Commissioner of Patents and Trademarks